United States Patent [19]

Yokozeki et al.

[11] Patent Number: 5,179,009
[45] Date of Patent: Jan. 12, 1993

[54] PROCESS FOR PRODUCING L-ASPARTYL-L-PHENYLALANINE AND ITS DIKETOPIPERAZINE

[75] Inventors: Kenzo Yokozeki; Naoki Usui; Toshihide Yukawa; Yoshiteru Hirose; Koji Kubota, all of Kawasaki, Japan

[73] Assignee: Ajinomoto Co., Inc., Tokyo, Japan

[21] Appl. No.: 707,306

[22] Filed: May 29, 1991

Related U.S. Application Data

[63] Continuation of Ser. No. 918,059, Oct. 14, 1986, abandoned.

[30] Foreign Application Priority Data

Oct. 11, 1985 [JP] Japan .................. 60-226584
Aug. 29, 1986 [JP] Japan .................. 61-203030

[51] Int. Cl.$^5$ .................. C02P 21/02; C02P 17/10; C02P 1/04; C12N 9/78
[52] U.S. Cl. .................. 435/71.2; 435/68.1; 435/117; 435/227; 435/231; 435/170; 435/822; 435/121; 426/548

[58] Field of Search .................. 435/68.1, 71.2, 117, 435/121, 227, 231, 170, 822; 426/548

[56] References Cited

U.S. PATENT DOCUMENTS

| | | | |
|---|---|---|---|
| 4,088,649 | 5/1978 | Smith et al. | 426/537 |
| 4,384,004 | 5/1983 | Cea et al. | 426/548 |
| 4,430,349 | 2/1984 | Malone et al. | 426/548 |

*Primary Examiner*—Irene Marx
*Attorney, Agent, or Firm*—Oblon, Spivak, McClelland, Maier & Neustadt

[57] ABSTRACT

The present invention is directed to a process for producing L-aspartyl-L-phenylalanine and/or L-aspartyl-L-phenylalanine diketopiperazine comprising contacting and reacting a culture, cell or a cell-treated product of a microorganism capable of hydrolyzing DKP into AP or capable of performing intramolecular condensation of AP into DKP with DKP and/or AP, in an aqueous medium.

13 Claims, No Drawings

PROCESS FOR PRODUCING L-ASPARTYL-L-PHENYLALANINE AND ITS DIKETOPIPERAZINE

This application is a continuation of application Ser. No. 06/918,059 filed Oct. 14, 1986, now abandoned.

BACKGROUND OF THE INVENTION

1. Field of the Invention

The present invention relates to L-aspartyl-L-phenylalanine (hereafter simply referred to as "AP") which is a precursor of L-aspartyl-L-phenylalanine methyl ester (hereinafter simply referred to as "APM"). APM is a dipeptide sweetener that has attracted attention in recent years.

2. Discussion of the Background

Known methods for the synthesis of a dipeptide utilizing a microorganism or an enzyme involve a process which comprises the introduction of appropriate protective groups to functional groups which are not involved in the condensation reaction of the two amino acids to restrict the location of the condensation reaction. A microorganism or an enzyme which is capable of synthesizing a peptide bond between these amino acid derivatives is then used to obtain the condensation products followed by removal of the superfluous protective groups from the condensation products to give the product dipeptide. Using this process, a satisfactory yield is obtained but the introduction and removal of the protecting groups is required. Thus, expensive protecting groups are needed and unnecessary complicated reaction steps are required.

For the biochemical syntheses of APM, there are known, for example, processes which comprise using a benzyloxy group (—Z) as a protective group for the amino group of aspartic acid and condensing N-benzyloxy-L-aspartic acid and phenylalanine methyl ester by the action of an endo-type protease. These processes involved the drawbacks described above.

Alternatively, processes for biochemical synthesis that require no protective groups in the synthesis of APM are also known (see Published Unexamined Japanese Patent Application 126796/83). Processes of this type do not require protective groups but the yield is poor and there is a problem in the synthesis of APM.

On the other hand, in the chemical synthesis of AP, it is necessary to use L-aspartic acid and L-phenylalanine, in order to produce sweet APM. This is because only L-aspartyl-L-phenylalanine methyl ester (APM), composed of only L-amino acids, is sweet among the four optical isomers of aspartyl-phenylalanine.

A good method for the separation of these four optical isomers was unknown to date so that DL-amino acids which were less expensive than L-amino acids could not be used as raw materials.

In addition, in order for the reaction to proceed, it is necessary to shift the reaction equilibrium toward the disadvantageous condensation side for the synthesis of AP. In the enzymatic condensation of L-aspartic acid and L-phenylalanine, it is necessary to remove AP from the reaction system to shift the synthesis equilibrium reaction toward the synthesis of AP. For this reason, processes utilizing these condensation reactions remove AP either by adsorbing the AP produced onto ion exchange resins, or by incorporating a precipitating agent in such a manner that AP becomes selectively insoluble.

These prior art processes have several serious defects, namely poor yields in conventional biochemical syntheses requiring no protecting groups and the use of expensive protecting group reagents and unnecessary reaction steps in processes involving protection of functional groups.

SUMMARY OF THE INVENTION

Accordingly, one object of the present invention is to provide a process for producing AP which does not require the use of expensive protecting group reagents or reaction steps involved in the protection of functional groups.

A second object of the invention is to provide a process for producing AP in high yield without the use of protecting groups.

A further object of the invention is to provide a novel process for synthesizing AP and for producing inexpensive APM with good efficiency on an industrial scale.

These objects and other objects of the invention which will become apparent from the following specification have been achieved by the present process for producing AP which comprises contacting a culture, cell or a cell-treated product of a microorganism with L-aspartyl-L-phenylalanine diktopiperazine in an aqueous medium, wherein said culture, cell or cell-treated product of a microorganism is capable of hydrolyzing L-aspartyl-L-phenylalanine diketopiperazine into L-aspartyl-L-phenylalanine.

The process of the present invention also comprises a process for producing L-aspartyl-L-phenylalanine diketopiperazine, which comprises contacting a culture, cell or a cell-treated product of a microorganism with L-aspartyl-L-phenylalanine in an aqueous medium, wherein said culture, cell or cell-treated product of a microorganism is capable of performing intramolecular condensation of L-aspartyl-L-phenylalanine to produce L-aspartyl-L-phenylalanine diketopiperazine.

DETAILED DESCRIPTION OF THE PREFERRED EMBODIMENTS

AP can be converted into APM by simple methyl esterification. The present invention is directed to a process for producing AP and more particularly, to a process for producing AP from L-aspartyl-L-phenylalanine diketopiperazine (hereafter simply referred to as "DKP").

The above-described reaction is an equilibrium reaction and, it is also possible, therefore, to synthesize DKP from AP by the reverse reaction. DKP is also an important substance as an APM precursor. After chemical synthesis of AP, it can be converted into DKP. In this way optically active AP can be separated from, for example, D-amino acid-contaminated aspartyl-phenylalanine in the reaction mixture and the optically active AP thus easily obtained.

It is also possible to increase the yield by using a microorganism capable of performing intramolecular condensation of AP to convert it into DKP. Since the process uses an equilibrium reaction system that is extremely disadvantageous for the synthesis of AP, e.g., direct binding of aspartic acid and phenylalanine using an enzyme, the AP produced in trace amounts is converted into DKP and the equilibrium is shifted toward the synthesis side.

It has been found that the hydrolysis of DKP occurs at a specific position and that the reverse reaction can be used to produce AP as shown in the reaction below.

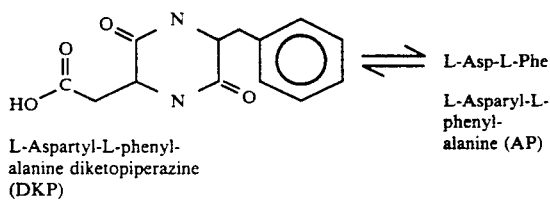

L-Aspartyl-L-phenyl-alanine diketopiperazine (DKP) ⇌ L-Asp-L-Phe L-Asparyl-L-phenyl-alanine (AP)

Nonlimiting examples of microorganisms which can be used in the present invention include the following:
Streptomyces flavovirens IFO 3197
Streptomyces parvulus AJ 9037 FERM-P 8920 FERM BP 1168
Achromobacter lacticum AJ 2394 FERM-P 7401
Agrobacterium tumefaciens ATCC 4452
Alcaligenes faecalis AJ 2565 FERM-P 8460
Bacillus circulans ATCC 9966
Enterobacter agglomerans ATCC 12287
Erwinia amylovora FERM-P 7056
Flavobacterium rhenanum AJ 2468 FERM-P 8459
Micrococcus varians ATCC 399
Serratia marcescens AJ 2763 FERM-P 8461
Xanthomonas citri AJ 2797 FERM-P 8462

To allow these microorganisms to act on DKP or AP, the microorganisms are cultured and the culture solution or cells of the microorganisms or cell-treated products are contacted with DKP or AP in aqueous media.

Media for culturing the above-described microorganisms are ordinary media containing ordinary carbon sources, nitrogen sources and inorganic ions. Additional incorporation of organic trace nutrients such as vitamins, amino acids, etc., often give preferred results.

As the carbon sources, carbohydrates such as glucose, sucrose, etc.; organic acids such as acetic acid, alcohols and others can appropriately be employed. As the nitrogen sources, ammonia gas, ammonia water, ammonium salts and others can be used. As the inorganic ions, magnesium ions, phosphate ions, potassium ions, iron ions and others can appropriately be employed, if necessary.

Culturing is carried out for 1 to 30 days under aerobic conditions while controlling pH and temperatures to appropriate ranges of 2 to 8 and 15° to 30° C., respectively.

To allow the culture solution, cells or cell-treated products of the microorganisms to act on DKP or AP in aqueous media, the cells or cell-treated products may be dissolved or suspended in the aqueous media containing DKP or AP and the aqueous media may be stirred for a short period of time or allowed to settle, while controlling the temperature to a preferred range of 10° to 70° C.

In the reaction which forms AP from DKP, the amount of DKP used is not particularly restricted but in the case of a batch system, the amount is generally approximately 0.01 to 2.0M, preferably 0.01 to 1.0M.

In the reverse reaction of producing DKP from AP, the amount of AP used is not particularly limited but in the case of a batch system, it is generally approximately 0.00001 to 2.0M, preferably 0.01 to 1.0M.

DKP or AP may also be added in portions as the reaction proceeds.

The reaction is conducted generally in the aqueous medium at temperatures of 10° to 60° C., preferably 20° to 40° C.

When using bacterial cells, the culture solution containing the cells may also be used as it is. Alternatively, the cells may be separated from the culture solution and used after washing or even without washing.

Appropriate cell-treated products include mechanically ground cells; cells treated with ultrasound; freeze dried cells; cells dried with acetone; cells treated with enzymes such as lysozyme, etc.; cells treated with surfactants, toluene, etc; protein fractions of the cells; immobilized products thereof and others.

To obtain such bacterial cells, the foregoing media and methods for culture can be adopted without modification.

Upon culture of the microorganism, cells having a high capability of producing AP from DKP or DKP from AP may sometimes be obtained by incorporating a small quantity of DKP or AP or both in the media.

In the equilibrium reaction for biochemical condensation of L-aspartic acid and L-phenylalanine, methods are generally adopted for removing the AP produced from the reaction system (e.g., treatment with ion exchange resin; a precipitating agent, extraction with a solvent, conversion using a reaction specific to AP, etc.) to accelerate the reaction toward the condensation side. These methods can also be used in the present invention by utilizing the conversion of DKP AP. Namely, the reaction can be accelerated toward the condensation side by incorporating microorganisms capable of converting AP to DKP or treated products thereof (as described hereinbefore). These microorganisms may be added by portions into the aforesaid equilibrium reaction systems at the initial stage of the reaction or during the course of the reaction. Various conditions for conversion from AP to DKP in this case may be those following the conditions described above.

Other features of this invention will become apparent in the course of the following descriptions of exemplary embodiments which are given for illustration of the invention and are not intended to be limiting thereof.

EXAMPLES

Example 1

Into a 500 ml flask was charged 50 ml of medium containing 1.0 g/dl of polypeptone, 1.0 g/dl of yeast extract, 0.3 g/dl of $K_2HPO_4$, 0.1 g/dl of $KH_2PO_4$, 0.05 g/dl of $MgSO_4.7H_2O$ and 0.5 g/dl of DKP (pH 7.0) followed by sterilization at 115° C. for 15 minutes.

The cultures obtained from the microorganisms shown in Table 1 which had been cultured at 30° C. for 2 days in bouillon-agar medium were inoculated in the above-described medium by one platinum loop each followed by culturing at 30° C. for 2 days. From these culture solutions, cells were taken out by filtration. After washing once with the same amount of physiological saline, the cells were collected.

These bacteria were added to 100 ml of a 0.1M Tris-HCl buffer (pH 8.0) containing DKP (2.0 g/dl) in a concentration of 1.0 g/dl, respectively, followed by reacting at 30° C. for 2 hours. The amounts of AP produced for each bacteria are shown in Table 1.

TABLE 1

| Strain | Produced mg/dl |
| --- | --- |
| Streptomyces flavovirens IFO 3197 | 450 |
| Achromobacter lacticum AJ 2394 FERM-P 7401 | 30 |

TABLE 1-continued

| Strain | Produced mg/dl |
| --- | --- |
| Agrobacterium tumefaciens ATCC 4452 | 65 |
| Alcaligenes faecalis AJ 2565 FERM-P 8460 | 35 |
| Bacillus circulans ATCC 9966 | 70 |
| Enterobacter agglomerans ATCC 12287 | 30 |
| Erwinia amylovora FERM-P 7056 | 45 |
| Flavobacterium rhenanum AJ 2468 FERM-P 8459 | 70 |
| Micrococcus varians ATCC 399 | 35 |
| Serratia marcescens AJ 2763 FERM-P 8461 | 40 |
| Xanthomonas citri AJ 2797 FERM-P 8462 | 65 |

EXAMPLE 2

Streptomyces flavovirens IFO 3197 which had been cultured, taken out and washed in a manner similar to Example 1 was reacted at 30° C. for 48 hours using the reaction solution as in Example 1. The amount of AP produced in this case was 420 mg/dl. L-Asp and L-Phe obtained by further decomposition of the AP produced were produced in amounts of 43 mg/dl and 57 mg/dl, respectively.

EXAMPLE 3

Microorganisms shown in Table 2 were cultured in a manner similar to Example 1 to give bacterial cells.

These cells were added to 100 ml of a 0.1M phosphate buffer (pH 6.0) containing AP (1.0 g/dl) in a concentration of 1.0 g/dl, respectively, followed by reacting at 30° C. for 2 hours. The amounts of DKP produced are shown in Table 2.

TABLE 2

| Strain | Produced mg/dl |
| --- | --- |
| Streptomyces flavovirens IFO 3197 | 820 |
| Achromobacter lacticum AJ 2394 FERM-P 7401 | 15 |
| Agrobacterium tumefaciens ATCC 4452 | 20 |
| Alcaligenes faecalis AJ 2565 FERM-P 8460 | 10 |
| Bacillus circulans ATCC 9966 | 10 |
| Enterobacter agglomerans ATCC 12287 | 15 |
| Erwinia amylovora FERM-P 7056 | 10 |
| Flavobacterium rhenanum AJ 2468 FERM-P 8459 | 25 |
| Micrococcus varians ATCC 399 | 10 |
| Serratia marcescens AJ 2763 FERM-P 8461 | 20 |
| Xanthomonas citri AJ 2797 FERM-P 8462 | 15 |

EXAMPLE 4

Streptomyces flavorings IFO 3197 was produced in a manner similar to Example 1, 1 g of which was suspended in 4 ml of deionized water. After ice cooling, 750 mg of acrylamide and 45 mg of methylenebisacrylamide were added. After oxygen was purged by introducing nitrogen gas, 3.5 mg of ammonium persulfate and 8 µl of N,N'-dimethylaminopropionitrile were added and the mixture was allowed to settle with ice cooling. After one hour, the cell-containing gel was passed through a metal mesh of 50 mesh and washed with physiological saline to prepare a gel-immobilized product. The immobilized product, 2 g, was added to the reaction solutions obtained in a manner similar to Examples 1 and 3, respectively, followed by reaction at 30° C. for 2 hours. The amounts of AP and DKP produced in this case were 370 mg/dl and 700 mg/dl, respectively.

EXAMPLE 5

Streptomyces parvulus AJ 9037 FERM BP-1168 or Streptomyces flavovirens IFO 3197 cultured, collected and washed in a manner similar to Example 1 was added to 100 ml each of a 0.1M Tris-HCl buffer (pH 8.0) and 0.1M carbonic acid buffer (pH 9.8) containing DKP (2.0 g/dl) in a concentration of 5 g/dl, respectively, followed by reacting at 30° C. for 10 hours. The results obtained are shown in Table 3.

TABLE 3

| | Amount of AP Produced (g/dl) | |
| --- | --- | --- |
| Strain | pH 8.0 | pH 9.8 |
| Streptomyces parvulus AJ 9037 FERM-P 8920 FERM BP-1168 | 0.22 | 0.85 |
| Streptomyces flavovirens IFO 3197 | 0.43 | 0 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing L-aspartyl-L-phenylalanine, which comprises:

contacting a microorganism selected from the group consisting of Streptomyces flavovirens IFO accession no. 3197, Achromobacter lacticum FERM-P accession no. 7401, Agrobacterium tumefaciens ATCC accession no. 4452, Alcaligenes faecalis FERM-P accession no. 8460, Bacillus circulans ATCC accession no. 9966, Enterobacter agglomerans ATCC accession no. 12287, Erwinia amylovora FERM-P accession no. 7056, Flavobacterium rhenanum FERM-P accession no. 8459, Micrococcus varians ATCC accession no. 399, Serratia marcescens FERM-P accession no. 8461 and Santhomonas citri FERM-P accession no. 8462, with L-aspartyl-L-phenylalanine diketopiperazine in an aqueous medium under aerobic conditions, a pH of about 2-8 and a temperature of about 20°-40° C. for a time sufficient to produce L-aspartyl-L-phenylalanine, wherein said microorganism enzymatically hydrolyzes L-aspartyl-L-phenylalanine diketopiperazine into L-aspartyl-L-phenylalanine and recovering the L-aspartyl-L-phenylalanine product.

2. The process of claim 1, wherein said contacting is for 1-30 days.

3. The process of claim 1, wherein said microorganism is Streptomyces flavovirens IFO accession no. 3197.

4. The process of claim 1, wherein said contacting is performed in a batch system.

5. The process of claim 1, wherein said microorganism is immobilized.

6. The process of claim 1, wherein said L-aspartyl-L-phenylalanine product is produced in an amount of 30–450 mg/dl.

7. The process of claim 6, wherein the amount of L-aspartyl-L-phenylalanine produced is 65–450 mg/dl.

8. A process for producing L-aspartyl-L-phenylalanine diketopiperazine, which comprises:

contacting a microorganism selected from the group consisting of *Streptomyces flavovirens* IFO accession no. 3197, *Achromobacter lacticum* FERM-P accession no. 7401, *Agrobacterium tumefaciens* ATCC accession no. 4452, *Alcaligenes faecalis* FERM-P accession no. 8460, *Bacillus circulans* ATCC accession no. 9966, *Enterobacter agglomerans* ATCC accession no. 12287, *Ervinia amylovora* FERM-P accession no. 7056, *Flavobacterium rhenanum* FERM-P accession no. 8459, *Micrococcus varians* ATCC accession no. 399, *Serratia marcescens* FERM-P accession no. 8461 and *Xanthomonas citri* FERM-P accession no. 8462, with L-aspartyl-L-phenylalanine under aerobic conditions, a pH of about 6 and a temperature of about 20°–40° C. for a time sufficient to produce L-aspartyl-L-phenylalanine diketopiperazine, wherein said microorganism performs the enzymatic intramolecular condensation of L-aspartyl-L-phenylalanine to produce L-aspartyl-L-phenylalanine diketopiperazine, and recovering the L-aspartyl-L-phenylalanine diketopiperazine product.

9. The process of claim 8, wherein said contacting is for 1–30 days.

10. The process of claim 8, wherein said microorganism is *Streptomyces flavovirens* IFO accession no. 3197.

11. The process of claim 8, wherein said contacting occurs in a batch system.

12. The process of claim 8, wherein the amount of L-aspartyl-L-phenylalanine diketopiperazine produced is 10–820 mg/dl.

13. The process of claim 8, wherein said microorganism is immobilized.

* * * * *